United States Patent [19]
Urza

[11] Patent Number: 5,377,532
[45] Date of Patent: Jan. 3, 1995

[54] METHOD AND SYSTEM FOR IN-LINE DETECTION OF MOISTURE IN URANIUM-CONTAINING POWDERS

[75] Inventor: Inaky J. Urza, Richland, Wash.

[73] Assignee: Siemens Power Corporation, Richland, Wash.

[21] Appl. No.: 128,402

[22] Filed: Sep. 29, 1993

[51] Int. Cl.$^6$ ............... G01N 33/22; G01N 27/00
[52] U.S. Cl. ............................... 73/73; 73/29.01
[58] Field of Search ............... 73/73, 29.01, 31.07

[56] References Cited

U.S. PATENT DOCUMENTS

| | | | |
|---|---|---|---|
| 3,367,850 | 2/1968 | Johnson | 422/83 |
| 4,934,182 | 6/1990 | Eggertsen et al. | 73/73 |
| 5,138,870 | 8/1992 | Lyssy | 73/29.01 |

*Primary Examiner*—Diego F. F. Gutierrez
*Attorney, Agent, or Firm*—Ira Lee Zebrak

[57] ABSTRACT

A moisture detection system for in-process nuclear fuel powder components includes a container within which the powder is located, a purge gas supply for providing a purge gas within the container, the purge gas contacting the powder and absorbing moisture therefrom, an off-gas line for transporting at least a portion of the purge gas after the purge gas contacts the powder and a moisture detector for determining the moisture in the purge gas. The moisture content of the purge gas provides an indication of the moisture content of the powder. A process for detecting moisture of an in-process nuclear fuel powder component includes the steps of supplying a purge gas, contacting the powder with the purge gas, transporting at least a part of the purge gas through an off-gas line, and measuring the moisture of the purge gas in the off-gas line, the moisture measurement providing a measure of moisture in the powder.

6 Claims, 5 Drawing Sheets

METHOD AND SYSTEM FOR IN-LINE DETECTION OF MOISTURE IN URANIUM-CONTAINING POWDERS

BACKGROUND OF THE INVENTION

1. Technical Field

The present invention relates to a method and a system for monitoring moisture in powdered material used to create nuclear fuel. More specifically, the present invention relates to in-line moisture detection for determining the moisture content of uranium-containing powders, including uranium dioxide powder.

2. Background Art

The moisture content of powders used to create nuclear fuels must be monitored closely. For example, for moderation control, the moisture content of uranium dioxide powder must not exceed 1.0% by weight to avoid any possibility of a criticality accident as required the United States Nuclear Regulatory Commission.

The current method for measuring moisture content of uranium dioxide powders requires removal of a sample from in-process powder. The sample is then analyzed using known techniques such as hydrolysis and hot extraction (total $H_2$).

While current methods for measuring the moisture content of the powder sample have resulted in accurate sample measurements, the sample moisture content is not always representative of the moisture of the entire in-process powder. For example, the sample may contain more or less moisture then the powder from which it was taken. In the event that the sample contains more moisture, unnecessary delays in future processing steps may result because the powder, based upon the results of the sample test, will be subjected to unnecessary additional drying procedures. In the event that the sample contains less moisture than is the case, powder having too much moisture may be passed on for future processing, leading to difficulties at later fuel processing stages.

Moreover, the method currently used requires that a sample be removed from the in-process powder and separately analyzed. Not only does such a method require additional time for removal, preparation and analysis of the sample, but handling of the sample to avoid contamination increases the cost relating to the powder processing. Furthermore, while the sample is taken, prepared and analyzed, the remaining powder remains idle until a moisture reading on the sample is received. The time required for removal, preparation and analysis of a sampling is approximately two to six hours. Accordingly, the in-process uranium dioxide powder remains idle for a significant period of time while the moisture content of the sample is measured. This time period is multiplied each time the sample fails to meet the moisture requirements because additional samples and testing must occur to verify that the powder is ready for further processing after additional steps are taken to remove the moisture in the powder.

Numerous attempts have been made in the past to develop a technique for rapid or in-process determination of moisture in uranium dioxide powder so as to avoid the sampling method currently in use. These efforts involved direct powder moisture measurement or indirect measurement of the atmosphere around the powder. In each case, the measurement process or configuration was not adequately sensitive or stable in the powder moisture range of 0–1.0 wt. %.

It is desirable to develop an accurate, reliable and stable measure of the overall moisture content of a nuclear fuel powder, such as uranium dioxide, particularly when the moisture content is in the range of 0–1.0% by weight.

OBJECTS AND SUMMARY OF THE INVENTION

Accordingly, one object of the invention is to provide for in-process moisture detection in nuclear fuel powders, thereby eliminating the time and cost associated with the removal, preparation and analysis of samples.

Another object of the invention is to provide accurate moisture detection representative of the entire powder rather than just a sample.

A further object of the invention is to provide moisture detection representative of the entire nuclear fuel powder which is accurate, reliable and stable, particularly in the powder moisture range of 0–1.0% by weight.

According to the present invention, the foregoing and other objects and advantages are attained by a moisture detection system for in-process nuclear fuel powder components comprising containing means within which the powder is located, purge gas supply means for providing a purge gas within the containing means, the purge gas contacting the powder and absorbing moisture therefrom, means for transporting at least a portion of the purge gas after the purge gas contacts the powder, and moisture detection means associated with the transporting means for measuring the moisture content of the purge gas and determining the moisture content of the powder. Furthermore, the foregoing and other objects and advantages are attained by a process for detecting moisture of an in-process nuclear fuel powder component comprising the steps of supplying a purge gas, contacting the powder with the purge gas so that the purge gas absorbs moisture therefrom, transporting at least a portion of the purge gas to moisture detection means, and, measuring the moisture of the purge gas to determine the moisture content of the powder.

The present invention, therefore, provides for moisture measurement which is representative of the entire product. In addition, the need to remove, prepare and analyze powder samples to obtain a moisture measurement is eliminated. Still other objects and advantages of the present invention will become readily apparent to those skilled in this art from the following detailed description, wherein the preferred embodiments of the invention are shown and described. As will be realized by one of ordinary skill, the invention is capable of other and different embodiments, and its several details are capable of modifications in various respects, all without departing from the invention. Accordingly, the drawings and description are to be regarded as illustrative in nature, and not as restrictive.

DETAILED DESCRIPTION OF THE PREFERRED EMBODIMENTS

Figure 1:
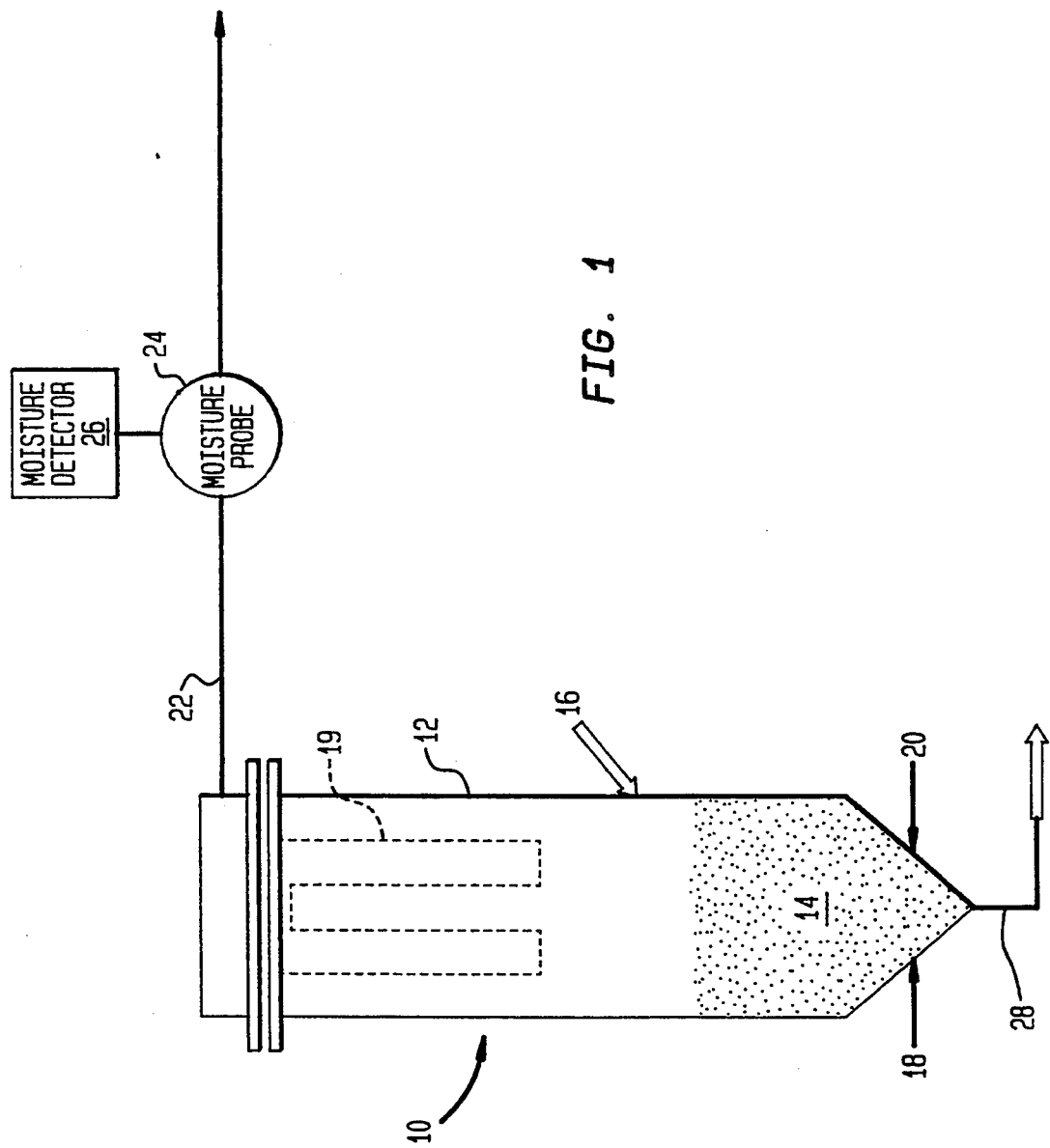
FIG. 1 is a plan view of a moisture detection system of a first embodiment of the present invention.

Referring to FIG. 1, a moisture detection system 10 according to the present invention includes a container 12 having uranium dioxide powder 14. Uranium dioxide powder 14 enters container 12 through an inlet 16. A fluidized bed may be formed within container 12 by supplying a fluidizing gas within container 12 through fluidizing gas inlet 18. Nitrogen or air may be used as the fluidizing gas. A filter assembly 19 is located within the container 12 to maintain the powder 14 within the container. Alternatively, a purge gas enters container 12 through purge gas inlet 20. For use as a purge gas, any of a number of commercially available gases may be utilized. Preferably nitrogen or dry air are used. Both the fluidizing gas and the purge gas contact the uranium dioxide powder 14 within the container 12. The fluidizing gas enters at a higher rate and volume to cause the uranium dioxide powder 14 to form a fluidized bed within container 12, while the purge gas would simply contact the powder as it passes through the container. When the gas contacts the powder it absorbs moisture therefrom.

Either of the purge gas or the fluidizing gas are transported from the container 12 through an off-gas line 22. A moisture probe 24 is placed within off-gas line 22 to contact the gas expelled through off-gas fine 22. The moisture probe 24 is connected to a moisture analyzer 26, which processes the reading taken by the moisture probe 24 to provide a moisture reading relating to the humidity of the gas in the off-gas line 22.

The moisture contained within the uranium dioxide powder 14 is absorbed by the gas which enters container 12 through inlet 18 or 20. The amount of water absorbed is related to the amount of actual free moisture in the powder. As the gas exits container 12 through off-gas line 22, moisture analyzer 26 and moisture probe 24 measure the moisture contained in the gas expelled. A correlation between the moisture content of the uranium dioxide powder 14 and the moisture in the gas in off-gas line 22 provides an indication of the moisture in the uranium dioxide powder 14, so as to confirm that the moisture content is at an amount less than the one percent (1.0%) by weight requirement.

The moisture probe 24 may be a thin film aluminum oxide moisture sensor based probe, however, various types of moisture probes may be employed. Such probes typically produce a millivolt signal proportional to the dew point of the gas. For uranium dioxide powder, the probe preferably has a dew point range of about −130° F. to 68° F. The hygrometric unit equivalent for this dew point range is 0.3 to 14,484 ppm water. Preferably, moisture analyzer 26 is an analyzer which correlates the sensor output to display a powder moisture content reading.

The detection system 10 is stable and relatively independent of temperature and flow conditions. For example, the container 12 does not require fluidization using the fluidizing gas. Merely supplying the purge gas through the purge gas inlet 20 is sufficient to obtain an accurate reading for operation of the system. This means that the system can be incorporated in various steps of the powder processing, including in intermediate powder storage vessels, or intermediate transport ducts, if desired.

Since the moisture detector 26 determines the moisture contained in the uranium dioxide powder 14 during processing, without pulling a powder sample for separate analysis, the uranium dioxide powder 14 can be removed from the container 12 through product outlet 28 for further processing, without delay.

Figure 2:
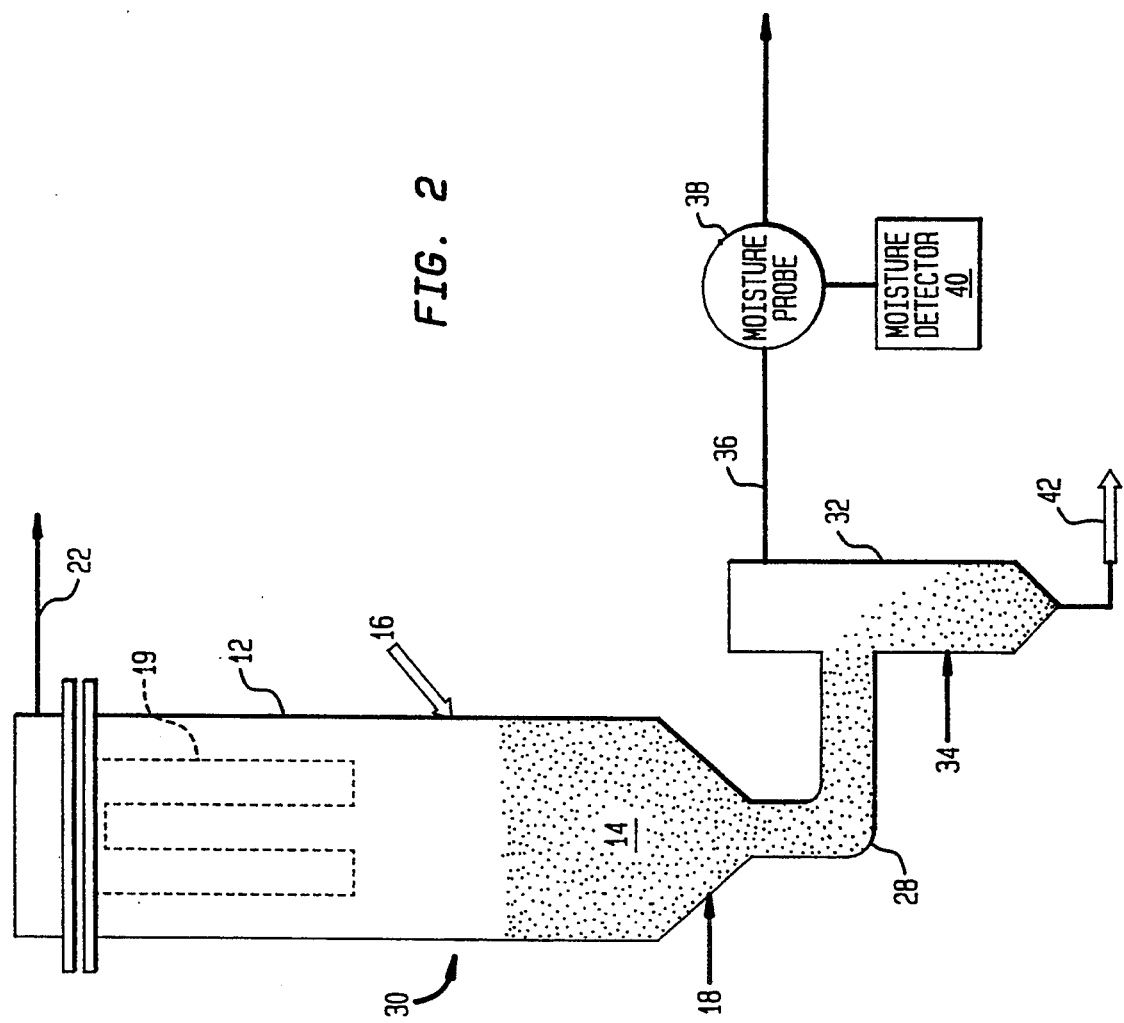
FIG. 2 is a plan view of a moisture detection system of a second embodiment of the present invention.

Referring to FIG. 2, an alternate embodiment of a moisture detection system 30 includes the container 12 for processing uranium dioxide powder 14. Uranium dioxide powder 14 enters container 12 through input 16. The container 12, in this instance may be representative of other uranium dioxide processing vessels, such as a calciner, dryer, or intermediate storage vessel. In this instance, as in FIG. 1, fluidizing gas may be supplied to container 12 through fluidizing gas inlet 18, and exit through off-gas line 22.

An outlet port 28 supplies the uranium dioxide powder 14 into a vessel 32, which may be used to collect the processed powder. Inlet 34 supplies a purge gas into the vessel 32. The purge gas contacts the falling uranium dioxide powder supplied from port 28. While contacting the falling dioxide powder, the purge gas absorbs moisture from the falling powder.

At least a part of the purge gas 34 then exits the vessel 32 through an off-gas line 36. A moisture probe 38 is placed within the off-gas line 36 to contact the purge gas flowing therethrough. A moisture detector 40 analyzes a signal from the probe and provides a reading relating the moisture contained in the gas to the moisture content of the powder. Uranium dioxide powder 14 is removed from vessel 32 through product port 42.

EXAMPLE

Figure 3:
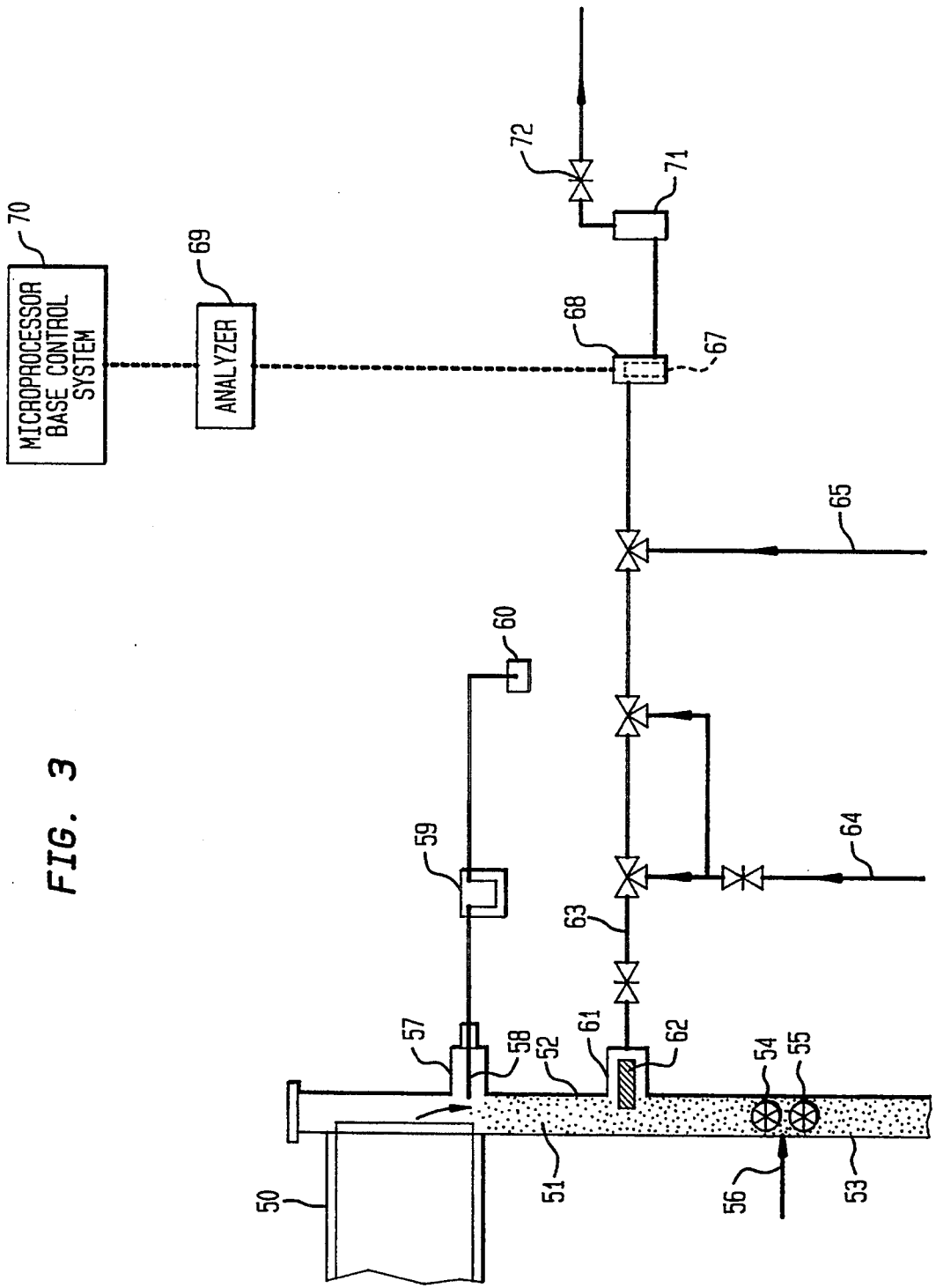
FIG. 3 is an illustration of a testing apparatus utilizing the present invention.

Tests were conducted to verify the advantages of the invention. Referring to FIG. 3, a calciner 50 deposits uranium dioxide powder 51 into a discharge chute 52. The chute exit end 53 incorporates a pair of rotary valves 54 and 55, which form an airlock to isolate the chute and powder. As the powder falls through the chute, nitrogen gas is fed through inlet 56 into the chute between the rotary valves. The nitrogen flows counter-current to the powder to pick up moisture from the powder.

The chute was modified to include an inlet 57 in which a pipe 58 is disposed. The pipe is connected via a metering pump 59 to a water supply tank 60.

Figure 4:
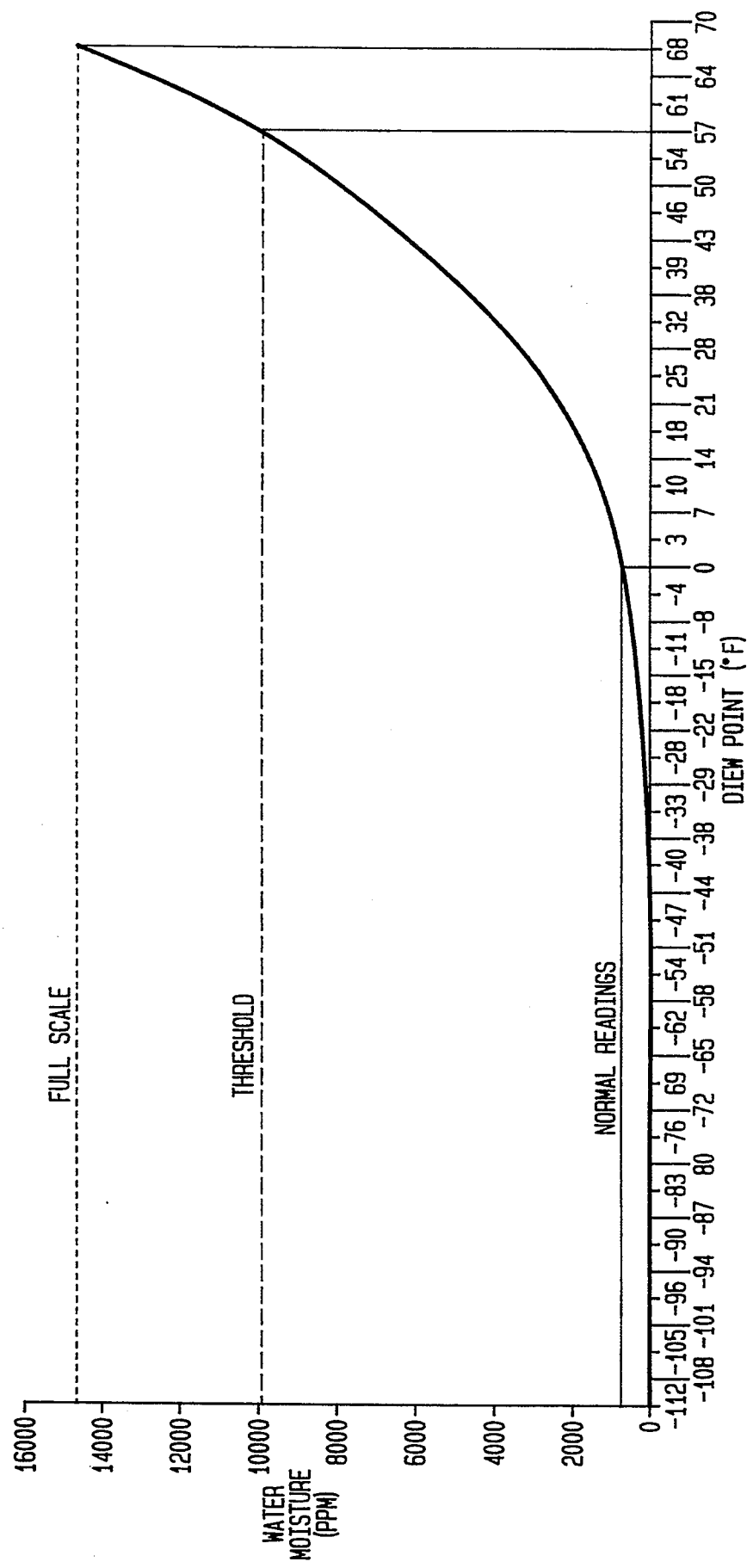
FIG. 4 is a graph illustrating the correlation between water content of a powder (normal and threshold readings) with atmosphere dew point.

The chute also has an outlet 61 within which a filter 62 is located. The filter is attached to a purge gas exhaust line 63. A second nitrogen supply 64 and appropriate valving were used to blow-back the filter 62 to prevent plugging. This nitrogen was also used as a zeroing gas to check system operation. Similarly, an air supply 65 was provided as a span gas, the air containing greater than 10,000 ppm water. A Panametrics model M22R thin film aluminum oxide moisture sensor 68 was located in a sample cell 67 and connected to a Panametrics analyzer 69. The sensor has a dew point range of −130° F. to 68° F., with a full scale reading being equivalent to 14,484 ppm water. FIG. 4 shows the hygrometric unit equivalent for this range as 0.3 to 14,484 ppm water. In turn, the analyzer was connected to a microprocessor based control system 70, for recording the data collected.

The flow through the line 63 was obtained by connecting the line to a vacuum source (not shown), the vacuum drawing at least a portion of the purge gas through the sample cell. The flow rate was monitored using a rotameter 71 and controlled using a manual metering valve 72. The flow rate of the sample stream was nominally 5 SCFH.

The moisture content of calcined powder is typically less than 1500 ppm. To test the system, from 5 to 100 ml of water were added with the metering pump the discharge chute, during each test. The dew point of the discharge chute atmosphere was continually monitored throughout each test. The powder from each test was placed in a bucket, tumbled and sampled for moisture analysis before, during and after each test.

The nitrogen supply 64 was used to determine zero readings. With nitrogen flowing through the sample cell, the sensor read between $-100°$ F. and $-50°$ F., equivalent to 1 to 40 ppm water by weight. Room air was periodically used to verify the system span, the sensor responding rapidly, within one minute, to the air which contained greater than 10,000 ppm water.

The results of nine moisture addition test results are shown in Table 1. The actual water addition for a single bucket, containing about 15 kg $UO_2$, ranged from 6700 ppm for a 100 ml water addition to 330 ppm for a 5 ml water addition. Sensor response was rapid with peak values observed within minutes. Duration of the peaks varied with the amount of water added and time of addition. The results shown in the Table confirm the inventive method's utility and sensitivity.

TABLE 1

| $H_2O$ ADDED RATE (ml/min) | TOTAL WATER ADDED (ml) | WATER ADDED TO POWDER (Equivalent) (ppm) | PEAK READING PPM $H_2O$ | BUCKET SAMPLE POWDER MOISTURE (PPM $H_2O$) | | |
|---|---|---|---|---|---|---|
| | | | | BEFORE TEST | DURING TEST | $H_2O$ CHANGE |
| 5 | 80 | 5333 | 11090 | 353 | 543 | 190 |
| 5 | 100 | 6667 | 8248 | 350 | 697 | 338 |
| 5 | 75 | 5000 | 5880 | 579 | 704 | 125 |
| 5 | 55 | 3667 | 14480* | 515 | 771 | 256 |
| 5 | 25 | 1667 | 14480* | 563 | 1021 | 458 |
| 5 | 5 | 333 | 6760 | 549 | 531 | 18 |
| 5 | 5 | 333 | 8330 | 557 | 625 | 68 |
| 7 | 35 | 2333 | 14480* | 1689 | 1783 | 94 |
| 10 | 10 | 667 | 14480* | 631 | 635 | 4 |

*INDICATES FULL SCALE READING

Figure 5:
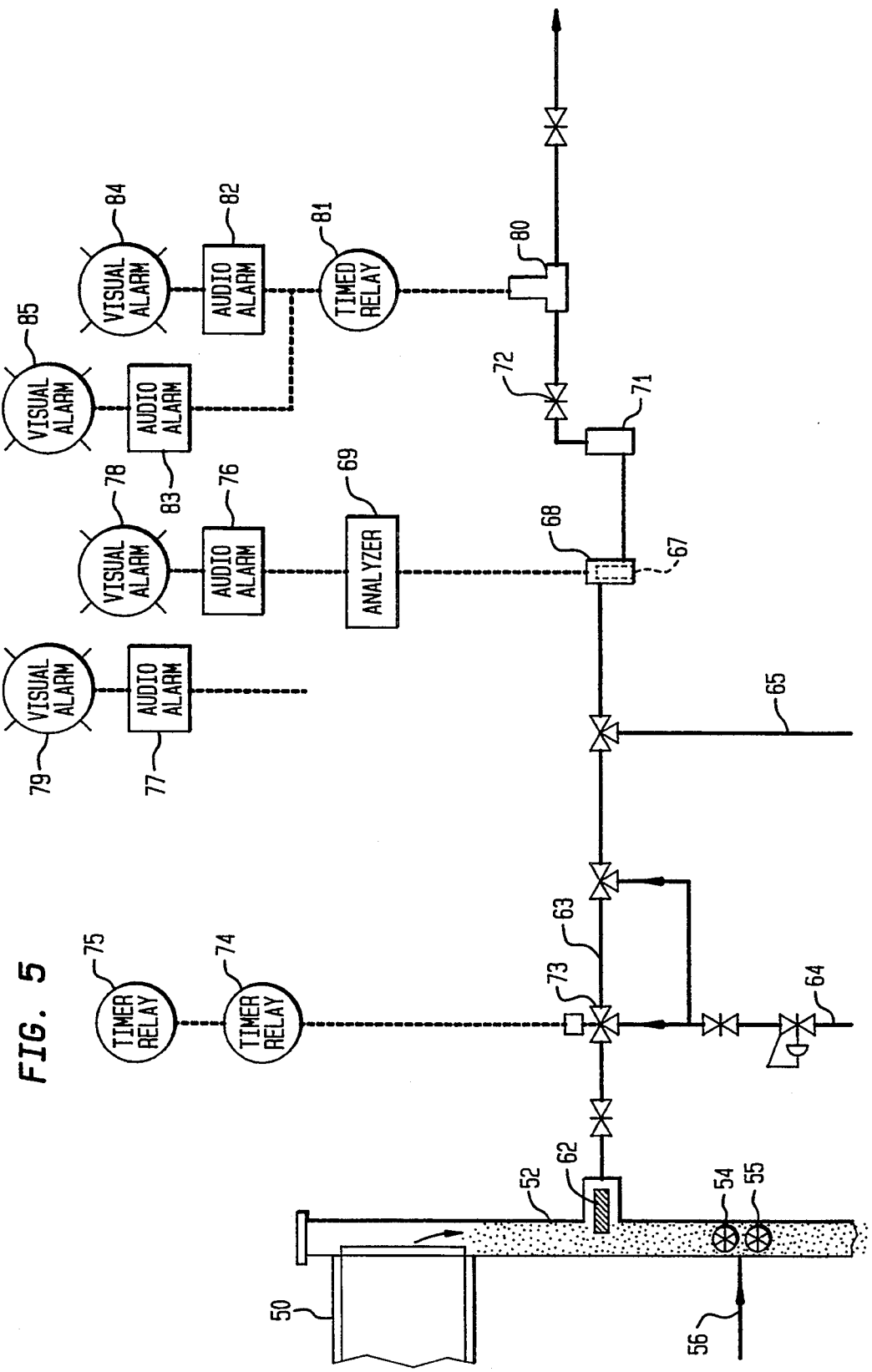
FIG. 5 is another alternative embodiment of the present invention.

Referring to FIG. 5, an alternative embodiment of the invention is shown, arranged for automatic in-process moisture detection. The arrangement is similar to that shown in FIG. 3, however, a solenoid valve 73 is incorporated in line 63 and is connected to a pair of timer relays 74 and 75 which provide for an automatic, periodic filter backflow.

In addition, the analyzer 69 connects to a pair of audio alarms, 76 and 77, one local and one remote, and a pair of visual alarms, 78 and 79, similarly arranged. These alarms are activated when a high moisture content is sensed, so that an operator is immediately notified.

A flow switch 80 is located in the line 63 and connected to a timed relay 81, the relay connected to another pair of audio alarms, 82 and 83, and visual alarms 84 and 85. The flow switch detects low flow conditions which may result from a plugged filter, or loss of vacuum.

Such a system provides for immediate detection of a high powder moisture content without requiring the product to be sequestered, sampled, and held pending powder analysis. This facilitates conversion to a continuous process as the uranium dioxide powder can move immediately to the next process step.

While preferred embodiments of the present invention have been shown and described it will be understood by those skilled in the art that various changes and modifications could be made without varying from the scope of the present invention.

What is claimed is:

1. A moisture detection system for in-process nuclear fuel powder components comprising:
    containing means having a nuclear fuel powder therein;
    purge gas supply means for providing a purge gas within said containing means, said purge gas contacting the powder;
    transport means connected to said containing means for transporting at least part of said purge gas therethrough, after said purge gas contacts the powder; and,
    moisture detection means for measuring the moisture in said transported purge gas, said measurement of moisture correlating to a measure of overall moisture in said powder wherein the purge gas is a fluidizing gas fluidizing the powder within said containing means.

2. The moisture detection system of claim 1 wherein said moisture detection means comprises:
    a probe, said probe positioned within said transport means to contact the purge gas therein, said probe generating a signal corresponding to moisture content, and,
    moisture analyzer means connected to said probe, said moisture analyzer means using said probe signal to determine the moisture in said purge gas.

3. The moisture detection system of claim 2 wherein said probe is an aluminum oxide probe.

4. The moisture detection system of claim 1 wherein said nuclear fuel powder is uranium dioxide.

5. A process for detecting moisture of an in-process nuclear fuel powder component comprising the steps of:
    providing a nuclear fuel powder;
    supplying a purge gas;
    contacting the nuclear fuel powder with the purge gas so that the purge gas absorbs moisture therefrom;
    transporting at least part of said purge gas to moisture detection means; and,
    measuring the moisture of said transported purge gas, said measure of moisture correlated to a measure of overall moisture content of said powder, wherein the purge gas is supplied such that the purge gas fluidizes the powder to create a fluidized bed.

6. The process of claim 5 wherein said powder is uranium dioxide.

* * * * *